United States Patent [19]

Razdan et al.

[11] 4,025,516

[45] May 24, 1977

[54] PROCESS FOR THE PREPARATION OF (−)-6a,10a-TRANS-6a,7,8,10a-TETRAHYDRODIBENZO[B,D]-PYRANS

[75] Inventors: Raj Kumar Razdan, Belmont; Haldean Cloyce Dalzell, Weston, both of Mass.

[73] Assignee: The John C. Sheehan Institute for Research, Inc., Cambridge, Mass.

[22] Filed: Nov. 28, 1975

[21] Appl. No.: 636,132

Related U.S. Application Data

[63] Continuation-in-part of Ser. No. 589,742, June 24, 1975, abandoned.

[52] U.S. Cl. .................. 260/345.3; 260/619 D
[51] Int. Cl.$^2$ ........................ C07D 311/78
[58] Field of Search .................. 260/345.3

[56] References Cited

UNITED STATES PATENTS

| | | | |
|---|---|---|---|
| 3,560,528 | 2/1971 | Petrzilka | 260/345.3 |
| 3,668,224 | 6/1972 | Petrzilka | 260/345.3 |
| 3,734,930 | 5/1973 | Razdan et al. | 260/345.3 |

OTHER PUBLICATIONS

Cotton et al., "Advanced Inorganic Chemistry", pp. 267, 429, 430, 439 (1966).
Razdan et al., J. Amer. Chem. Soc., 96, 5860 (9/4/74).

*Primary Examiner*—James O. Thomas, Jr.
*Assistant Examiner*—Nicky Chan
*Attorney, Agent, or Firm*—Barbara Zitko Terris

[57] ABSTRACT

(−)-6a,10a-trans -1-Hydroxy-3-n-pentyl-6,6,9-trimethyl-6a,7,8,10a-tetrahydrodibenzo[b,d]pyran and related pyrans are prepared by a one-step process from (+)-p-mentha-2,8-dien-1-ol and substituted resorcinols. The pyrans produced by the process of this invention have useful pharmacological properties.

18 Claims, No Drawings

PROCESS FOR THE PREPARATION OF (−)-6A,10A-TRANS-6A,7,8,10A-TETRAHYDRODIBENZO[B,D]-PYRANS

The invention described herein was made in the course of work under a grant form the Department of Health, Education and Welfare.

CROSS-REFERENCE TO RELATED APPLICATION

This application is a continuation-in-part of copending U.S. application Ser. No. 589,742 filed June 24, 1975, now abandoned.

BACKGROUND OF THE INVENTION

Cannabis preparations in the form of marihuana, hashish, etc. have been known and used for many years for their psychoactive and therapeutic properties. The major active constituent of the resin which is exuded by the female plants of Cannabis sativa L. is (−)-6a,10a-trans-1-hydroxy-3-n-pentyl-6,6,9-trimethyl-6a,7,8,10a-tetrahydrodibenzo[b-d]pyran, also known as (−)-6a,10a-trans-Δ$^9$-tetrahydrocannabinol or Δ$^9$-THC. The structure and absolute configuration of this material was first reported by Gaoni et al. in J. Amer. Chem. Soc., 86, 1646 (1964). Since that time considerable research has been directed towards the preparation of this compound via a synthetic method, thereby eliminating the need to obtain the material by extraction from natural sources.

Because of the widespread use of Cannabis preparations all over the world, it has become necessary to study the pharmacology and toxicity of the active constituent, viz. Δ$^9$-THC in greater detail. In the past, attempts to study the pharmacological effects of this compound have been hampered by variations in the potency of the plant material. Accordingly, a supply of pure synthetic material is essential to carry out these studies as well as to enabale accurately reproducible dosages of the active ingredient to be used for its pharmacological properties.

One synthetic method of preparing Δ$^9$-THC is disclosed by Petrzilka in U.S. Pat. Nos. 3,560,224 and Petrizilka et al. in Helv. Chim. Acta, 52, 1102 (1969). The method of Petrzilka condenses (+)-p-mentha-2,8-den-1-ol and olivetol in the presence of an acid to give (−)-6a,10a-trans-Δ$^8$-tetrahydrocannabinol which is converted by a two-step process into the desired (−)-6a,10a-trans-Δ$^9$-tetrahydrocannabinol. The Petrizilka process can be represented as follows:

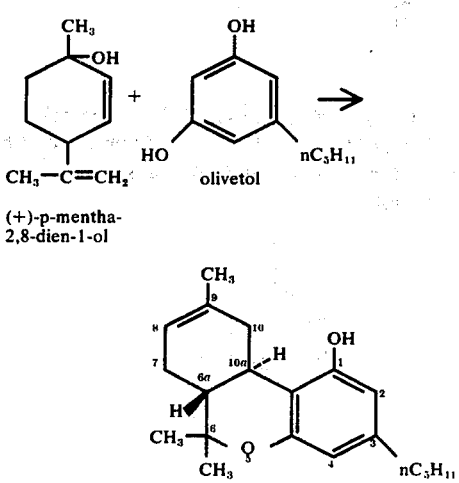

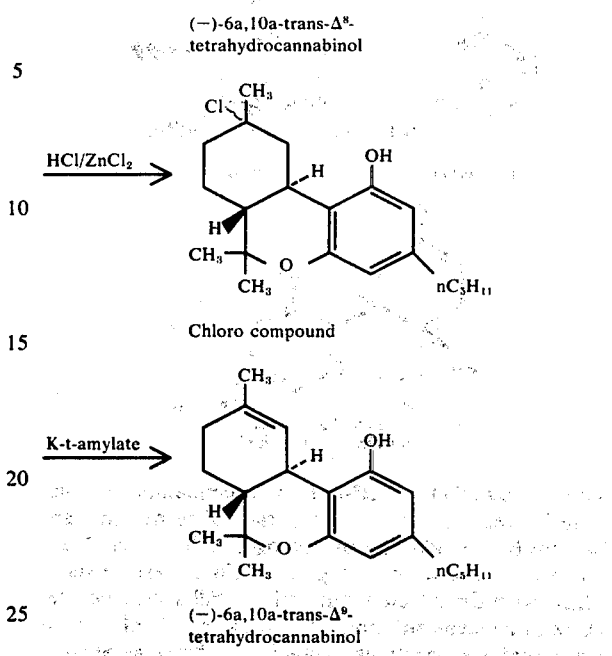

In Helv. Chim. Acta, 52, 1102 (1969), Petrzilka et al. have postulated the intermediacy of (−)-6a,10a-trans-Δ$^9$-tetrahydrocannabinol in the condensation reaction. They suggested that (+)-p-mentha-2,8-dien-1-ol and olivetol react to give (−)-6a,10a-trans-Δ$^9$-tetrahydrocannabinol, but the double bond is quickly isomerized to the more thermodynamically stable position in (−)-6a,10a-trans-Δ$^8$-tetrahydrocannabinol. Using a variety of acids, including boron trifluoride etherate in ether at room temperature and boron trifluoride etherate in benzene at 65°–70° C for 3 hours, they obtained (−)-6a,10a-trans-Δ$^8$-tetrahydrocannabinol but none of the Δ$^9$ isomer. In one case where 0.0005 N hydrogen chloride in refluxing ethanol was used, a small amount (1%) of Δ$^9$-THC was obtained accompanied by 2.4% of Δ$^8$-THC and 79% of unreacted starting material (Helv. Chim. Acta, 52, p. 1124).

The (−)-6a,10a-trans-Δ$^8$-tetrahydrocannabinol formed during the condensation reaction is separated from unwanted side-products by column chromatography. Treatment of the purified Δ$^8$-THC with hydrogen chloride in the presence of zinc chloride gives the chloro compound which is isolated and subsequently treated with potassium tert-amylate to yield the desired (−)-6a,10a-trans-Δ$^9$-tetrahydrocannabinol. If high purity (>95% pure by gas-liquid chromatography) Δ$^9$-THC is desired, the product must be purified by column chromatography and may also be distilled (Razdan et al., Experientia, 28, 121 (1972)).

Another synthesis of Δ$^9$-THC has been reported by Mechoulam et al. in J. Amer. Chem. Soc., 94, 6159 (1972). The Mechoulam synthesis first reacts (−)-verbenol with olivetol in the presence of boron trifluoride etherate or p-toluenesulfonic acid followed by boron trifluoride etherate to form (−)-6a,10a-trans-Δ$^8$-tetrahydrocannabinol. The reaction can be represented as follows:

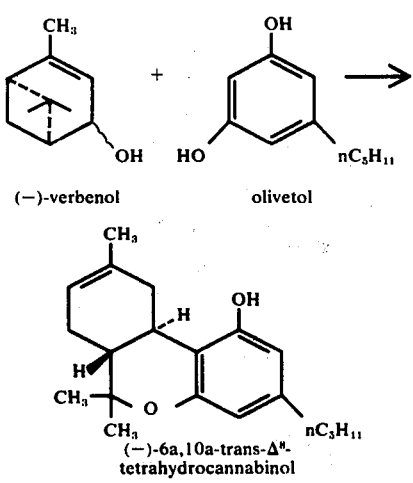

(−)-verbenol    olivetol

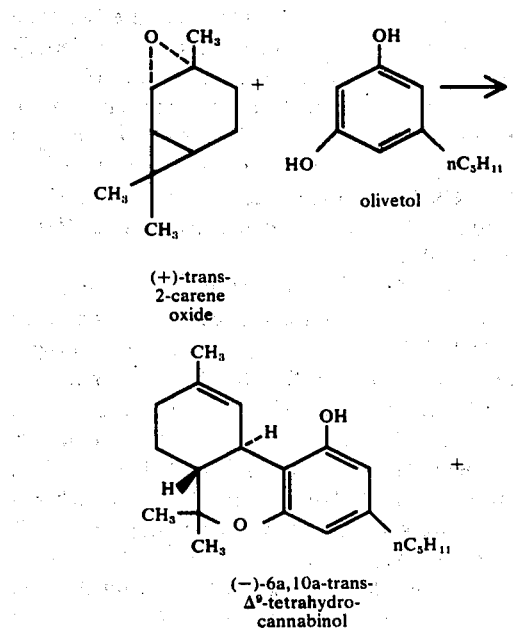

The (−)-6a,10a-trans-Δ⁸-tetrahydrocannabinol is then transformed to (−)-6a,10a-trans-Δ⁹-tetrahydrocannabinol by the addition of hydrogen chloride and subsequent elimination using potassium tert-amylate. Thus, both the Mechoulam and Petrzilka methods require three steps and involve at least two careful chromatographic separations to obtain (−)-6a,10a-trans-Δ⁹-tetrahydroccannabinol of high purity.

A single step synthesis of a cis and trans mixture of (−)-Δ⁹-tetrahydrocannabinol has been reported by Razdan and Handrick in U.S. Pat. No. 3,734,930 and Razdan and Handrick in J. Amer. Chem. Soc., 92, 6061 (1970). The synthesis is achieved by reaction (+)-trans-2-carene oxide and olivetol in the presence of boron trifluoride etherate or p-toluenesulfonic acid as represented below:

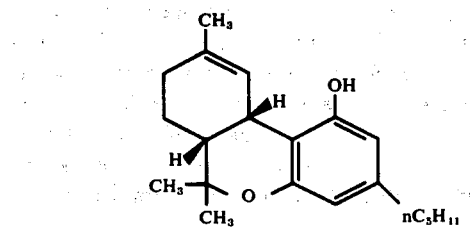

-continued
(−)-6a,10a-cis-Δ⁹-tetrahydrocannabinol

This synthesis avoids the problem of isomerization of the double bond to the Δ⁸ position but gives both the cis and trans isomers of (−)-Δ⁹-tetrahydrocannabinol as the major reaction products. Separation of the cis and trans isomers is difficult. Techniques such as preparative gas-liquid chromatography or high pressure-liquid chromatography must be employed to separate the isomers. Utilization of these techniques for preparation of large amounts of material is considered impractical at the present time. Thus, the carene oxide synthesis is limited to preparation of small quantities of (−)-6a,10a, -trans-Δ⁹-tetrahydrocannabinol.

Of the three syntheses of Δ⁹-THC described above, the Petrzilka and Mechoulam methods require three steps and two chromatographic separations. The Razdan synthesis from (+)-trans-2-carene oxide provides a mixture of cis and trans (−)-Δ⁹-tetrahydrocannabinol in one step but separation of the trans from the cis is difficult. Based on the availability of starting materials and ease of separation, the Petrilka process has been up to the present time the method of choice for preparation of (−)-6a,10a-trans-Δ⁹-tetrahydrocannabinol.

The present invention provides an improved method of preparing (−)-6a,10a-trans-Δ⁹-tetrahydrocannabinol, more particularly a one-step process for the preparation of (−)-6a,10a-trans-Δ⁹-tetrahydrocannabinol and related (−)-6a,10a-trans-1-hydroxy-6,6,9-trimethyl-6a,7,8,10a-tetrahydrodibenzo[b,d]pyrans wherein the desired compound are obtained in good yield and can be easily purified by simple column chromatography It also provides and improved method for making cannabidiols and related 2- and 4-(p-mentha-1,8-dien-3-yl)resorcinols.

SUMMARY OF THE INVENTION

In accordance with this invention, it has been found that compounds of the formula

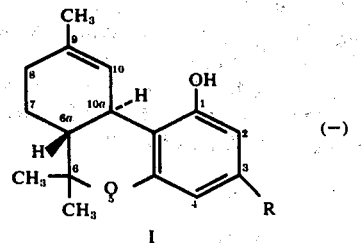

I wherein R is hydrogen or a straight or branched chain alkyl containing from 1 to 10 carbon atoms, can be synthesized by condensing a substituted resorcinol of the general formula

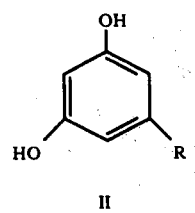

II wherein R is as above, with (+)-p-mentha-2,8-dien-1-ol of the formula

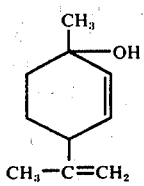

III in the presence of 0.04 to 0.40 mole per liter of an acid catalyst and an excess of a non-alkaline dehydrating agent.

It is a second aspect of this invention that compounds of the formulas

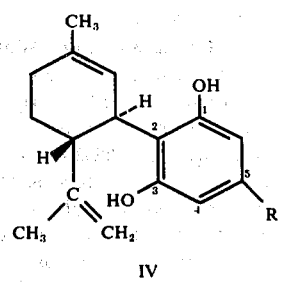

IV

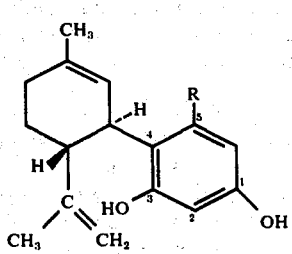

V wherein R is hydrogen or a straight or branched chain alkyl containing 1 to 10 carbon atoms, can be obtained by carrying out the condensation reaction between a resorcinol of Formula II wherein R is as above, and (+)-p-mentha-2,8-dien-1-ol of Formula III in the presence of 0.008 to 0.04 molar concentration of boron trifluoride and an excess of a non-alkaline dehydrating agent.

It is another aspect of this invention that compounds of Formula I, wherein R is hydrogen or a straight or branched alkyl containing 1 to 10 Carbon atoms, can be prepared by treating compounds of Formula V either alone or in admixture with compounds of Formula IV, wherein R is as above, with a Lewis acid catalyst.

In addition to producing $(-)$-6a,10a-trans-$\Delta^9$-tetrahydrocannabinol, the process of this invention is useful in the preparation of related pyrans where R is other than n-pentyl. The $(-)$-6a,10a-trans-$\Delta^9$-tetrahydrocannabinol has central nervous system activity and shows stimulatory and depressant properties depending on the dose administered. Included among the effects of this compound are sedative-hypnotic, analgesic, anti-glaucoma and anti-convulsant activities. the pyrans of Formula I where R is other than n-pentyl are useful in that they have a pharmacological profile that is qualitatively similar to that of the naturally occurring material.

The compound of Forula IV where R is n-pentyl shows anti-convulsant activity. The compounds of Formulas IV and V are useful in that they can be utilized for the preparation of compounds of Formula I by treatment of a compound of Formula IV or a compound of Formula V or a mixture of a compound of Formula IV and a compound of Formula V with an acid catalyst.

DETAILED DESCRIPTION

The numbering system used for fixing the position of substituents on the rings is shown in Formulas I, IV and V. In describing the steric arrangement of atoms or groups in the Formula, a solid line is used to represent a position above the plane of the drawing and a broken line indicates a position below the plane of the drawing. Throughout the application, $(-)$-6a,10a-trans-1-hydroxy-3-n-pentyl-6,6,9-timethyl-6a,7,8,10a-tetrahydrodibezo[b,d]pyran is also referred to as $(-)$-6a,10a-trans-$\Delta^9$-tetrahydrocannabinol or $\Delta^9$-THC, whereas $(-)$-6a,10a-trans-$\Delta^8$-tetrahydrocannabinol or $\Delta^8$-THC refers to $(-)$-6a,10a-trans-1-hydroxy-3-n-pentyl-6,6,9-trimethyl-6a,7,10,10a-tetrahydrodibenzo[b,d]pyran.

The term cannabidiols is used to refe to a mixture of the 2- and 4-(p-mentha-1,8-dien-3-yl)-olivetols.

As used herein, the term alkyl includes both straight and branched chain alkyl groups containing from 1 to 10 carbon atoms as illustrated by but not limited to methyl, ethyl, propyl, isopropyl, butyl, tert-butyl, n-pentyl, 3-pentyl, n-hexyl, 3,3-dimethyl-2-heptyl, 1,2-dimethylheptyl, n-nonyl and 2,3-dimethyl-2-oxtyl. In a preferred embodiment of the reaction, R is n-pentyl and the resorcinol of Formula II is 5-n-pentylresorcinol also known as olivetol. As disclosed in U.S. Pat. No. 3,576,798, the 5-alkyl-resorcinols of Formula II are conveniently prepared by methods generally known in the art comprising dehydration of a 3,5-di-lower -alkoxyphenyl alkyl carbinol, reduction of the resulting 3,5-di-lower-alkoxyphenylalkene, and hydriodic acid cleavage of the ether groups to the corresponding 5-alkylresorcinol. The starting carbinols in turn are prepared by reaction of an appropriate Grignard reagent with a 3,5-di-lower-alkoxybenzoic acid ester, amide, or 3',5'-di-lower-alkoxy-alkanophenone. Olivetol, orcinol (where R is methyl), and resorcinol (where R hydrogen) are commerically available.

In carrying out the process of this reaction either the cis or the trans isomers of (+)-p-mentha-2,8-dien-1-ol or a mixture of both isomers can be used. These materials are commerically available from Firmenich, Inc. of Switzerland. Alternatively, the (+)-p-mentha-2,8-dien-1-ol can be prepared by the method of Schenk el al., Ann. Chem., 674,93 (1964).

In compounds of Formula I are prepared by reacting approximately equimolar quantities of a substituted resorcinol of Formula II and (+)-p-mentha-2,8-dien-1-ol of Formula III in the presence of 0.04 to 0.40 mole per liter of an acid catalyst and an excess of a non-alkaline dehydrating agent. Using preferred conditions described later herein, the reaction can be conveniently carried out in 1.5 hr. In general, the time required for formation of a compound of Formula I will be dependent on the concentration of a given acid catalyst and the reaction temperature. A discussion of the rates of formation and mechanism of the reaction is contained in (Razdan et al.) J. Amer. Chem. Soc., 96, 5860 (September 1974). After the compound of Formula I has formed, the reaction is stopped by the addition of a basic substance such a sodium carbonate or sodium bicarbonate to quench the acid catalyst. The use of sodium or sodium bicarbonate is not critical, and other basic substances which will quench the acid catalyst but are otherwise non-reactive can also be used. The inorganic materials are removed from the reaction mixture by filtration, and the filtrate is evaporated to give a residue from which the desired pyran is isolated by column chromatography. Other techniques which are useful for the purification of these compounds are preparative thin-layer chromatography, preparative gas-liquid chromatography, and high pressure-liquid chromatography.

The presence of a non-alkaline dehydrating agent is essential in carrying out the one-step process for the preparation of compounds of Formula I. Any conventional material which has the ability to readily combine with a molecule of water, and is non-alkaline and otherwise chemically inert can be used. Agents useful in the practice of this invention include calcium sulfate, magnesium sulfate, sodium sulfate, calcium chloride, aluminum oxide, silica and molecular sieves such as those formed from potassium aluminum silicate. The reaction is advantageously carried out by throughly mixing an excess of the non-alkaline dehydrating agent with the reactants so as to efficiently remove water as it is formed during the reaction. By excess is meant a quantity which is sufficient to react with the water formed during the condensation and any water which is present in the solvent.

In carrying out the reaction, any conventional inert organic solvent such as petroleum ether, diethyl, benzene, toluene, tetrahydrofuran, dioxane and halogenated aliphatic or aromatic hydrocarbons such as methylene chloride, chloroform, carbon tetrachloride and bromobenzene can be used. When ethers such as diethyl ether, dioxane and tetrahydrofuran are used, a higher concentration of acid catalyst may be required. The use of chlorinated hydrocarbons is preferred.

The reaction between a resorcinol of Formula II and (+)-p-mentha-2,8-dien-1-ol is carried out in the presence of an acid catalyst. The use of boron trifluoride is preferred, although other Lewis acids such as aluminum chloride, zinc chloride, stannic chloride and antimony pentafluoride can also be utilized. A convenient form for the use of boron trifluoride is boron trifluoride complexed with diethyl ether, also known as boron trifluoride etherate. Boron trifluoride can also be dissolved in inert anhydrous solvents, and the use of such solutions would also be suitable. Protonic acids such as p-toluenesulfonic, methanesulfonic and trifluoroacetic acid can also be used but the yields are generally lower. The concentration of acid catalyst used in the reaction is expressed in moles of acid per liter of reaction solvent.

The process of this invention makes possible a one-step synthesis of 6a,7,8,10a-tetrahydrodibenzo[b,d]pyrans of Formula I, including $\Delta^9$-THC. In all cases, the reaction does not yield the compounds of Formula I exclusively, but under optimal conditions of dehydrating agent, acid catalyst concentration and reaction temperature and time, it is possible to obtain compounds of formula I that are free of the $\Delta^8$ isomer. Using conditions described herein, the process of this invention provides a method for the syntheiss of compounds of Formula I where the amount of compounds of Formula I compared to other products is approximately 1 to 1 or more.

The one-step process is conveniently carried out in the temperature range of $-20°$ to $+25°$ C at a molar concentration of boron trifluoride of greater than 0.04 and up to 0.40 M. At a concentration of 0.008 to 0.04 M of boron trifluoride at 0° C, the compounds of Formulas IV and V are obtained and the preparation of compounds of Formula I can be carried out in two stages. Thus, the intermediate 2- and 4-(p-mentha-1,8-dien-3-yl) resorcinols of Formulas IV and V which are first obtained at an acid catalyst concentration of 0.008 to 0.04 M are treated in the second stage with an acid catalyst at a concentration greater than 0.04 M. Within the limits of $-20°$ to $+25°$ C and 0.04 to 0.40 M concentration of boron tifluoride, the rate of formation of a compound of Formula I can be controlled by changing the parameters of acid concentration and reaction temperature. At higher temperature such as 25° C, a lower concentration of boron trifluoride such as 0.06 M can be used, whereas at a temperature of $-10°$ C, a concentration of 0.2 M of boron trifluoride can be used to provide a convenient reaction time. When acid catalysts other than boron trifluoride are used, the rate of reaction can be similarly controlled by changing the acid concentration and reaction temperature. Techniques such as gas-liquid chromatography, thin-layer chromatography and nuclear magnetic resonance can be used to monitor the course of the reaction.

In a particularly preferred embodiment of the process for the one-step synthesis of compounds of Formula I, the reaction is carried out in methylene chloride with an excess of magnesium sulfate and 0.08 M of boron trifluoride etherate at a temperature of $-5°$ to $+5°$ C.

It is another aspect of the invention that a mixture of compounds of Formulas IV and V can be obtained in good yield by reacting (+)-p-mentha-2,8-dien-1-ol and a resorcinol of Formula II in the presence of 0.008 to 0.04 M boron trifluoride and a non-alkaline dehydrating agent. The reaction is carried out in the same manner as the reaction for the preparation of compounds of Formula I, and the solvent, reaction temperature and the non-alkaline dehydrating agent are the same as those described hereinabove. In a preferred embodiment, the reaction is carried out in methylene chloride with 0.008 M boron trifluoride etherate in the presence of excess magnesium sulfate at a temperature range of $-5°$ to $+5°$ C.

The compound of Formula IV where R is n-pentyl is a constituent of Cannabis and has been obtained by extraction from the natural plant material. The compounds of Formulas IV and V were R is hydrogen and n-pentyl have been prepared by the method of Petrzilka et al. as disclosed in Helv. Chim. Acta, 52, 1102 (1969). The Petrzilka method reacts olivetol and (+)-p-mentha-2,8-dien-1-ol using N,N-dimethylformamide dineopentyl acetal or weak acids, such as oxalic, picric or maleic, as the catalysts. The yields of compounds of Formulas IV and V (R is n-pentyl) and the amount of unreacted olivetol varied according to the different catalysts and workup procedure. When the reaction was carried out using N,N-dimethylformamide dineopentyl acetal, the following yields of isolated products (based on amount of olivetol charged in the reaction) where obtained: 25 percent of a compound of Formula IV, 35 percent of a compound of Formula V, 30 percent of unreacted olivetol and 5 percent of a compound formed by the reaction of two moles of (+)-p-mentha-2,8-dien-1-ol with olivetol. With N,N- dimethylformamide dienopentyl acetal, the sum of cannabidiols of Formulas IV and V is approximately 60 percent, as compared to the weak acid catalysts, where the sum of the cannabidiols was generally in the range of 40 to 58 percent of the yield of isolated products (Helv. Chim. Acta, 52, p. 1105 and 1119). Petrzilka et al. noted that the use of strong acids in this reaction gives rise to secondary reactions (Helv. Chim. Acta, 52, p. 1105).

We have found that compounds of Formulas IV and V can be prepared using a strong acid catalyst, viz. boron trifluoride at a concentration of 0.008 to 0.04 M in the presence of a non-alkaline dehydrating agent. When R is n-pentyl, the sum of compounds of Formulas IV and V is in the range of 70 to 75 percent or higher, with the relative amounts of each cannabidiol being related to the reaction time. Thus, after 1.5 hr at 0° C with 0.008 M boron trifluoride etherate, the reaction mixture contined 28 percent of a compound of Formula IV and 47 percent of a compound of Formula V, as well as 17 percent of unreacted olivetol. After 16 hr at the same temperature and concentration, the ratio of the cannabidiols was nearly 1 to 1, with 36 percent of the compound of Formula IV and 35 percent of the compound of Formula V.

We have found that preparation of cannabidiols by the method of this aspect of the invention is advantageous in that the reaction between olivetol and (+)-p-mentha-2,8-dien-1-ol is more complete and less unreacted olivetol remains. The sum of the mixture of cannabidiols prepared by our process is in the range of 70 to 75 percent of higher, as compared to a yield of 60 percent obtained by the Petrzilka synthesis. As will be described below, a mixture of cannabidiols can be transformed to $(-)$-$6a,10a$-trans-$\Delta^9$-tetrahydrocannabinol, and both the compound of Formula IV and the compound of Formula V are converted. The cannabidiols produced by the process of this invention are particularly useful for conversion to $\Delta^9$-THC, since the increased yield of the cannabidiols mixture results in a higher yield of $\Delta^9$-THC.

The compounds of Formulas IV and V which are prepared by any of the procedures described above can be treated with a Lewis acid catalyst under anhydrous conditions to give a compound of Formula I. Gaoni and Mechoulam in Tetrahedron, 22, 1481 (1966) and J. Amer. Chem. Soc., 93, 217 (1971) have prepared a compound of Formula I where R is n-pentyl by treatment of a compound of Formula IV where R is n-pentyl using boron trifluoride etherate. Petrzilka et al. reported in Helv. Chim. Acta, 52, 1102 (1969) that reacting a compound of Formula V where R is n-pentyl with p-toluenesulfonic acid in benzene gives $(-)$-$6a,1$-$0a$-trans-$\Delta^8$-tetrahydrocannabinol. As described in (Razdan et al.) J. Amer. Chem. Soc., 96, 5860 (September 1974), we have found that compounds of Formula V or a mixture of compounds of Formulas IV and V can be converted to compounds of Formula I. the reaction can be carried out by combining a compound of Formula V or a mixture of compounds of Formulas IV and V with a Lewis acid catalyst in an inert solvent under anhydrous conditions. The solvent, concentration of Lewis acid catalyst, and temperature range are the same as those described hereinabove for preparation of a compound of Formula I from a resorcinol of Formula II and (+)-p-mentha-2,8-dien-1-ol. After the compound of Formula I has formed, the reaction is worked up in the same fashion as described herein-above, and the desired compound is isolated using chromatographic techniques. A preferred embodiment of this aspect of this invention is carried out in methylene chloride at a temperature of $-5°$ to $+5°$ C with 0.08 M boron trifluoride etherate.

The compound prepared by the process of this invention were analyzed by gas-liquid chromatography and identified on the basis of relative retention times of authentic samples and by the addition of autentic samples to the mixture. The samples were analyzed both silylated and unsilylated; the silylating agent used was bis(trimethylsilyl)trifluoroacetamide. After purification of the compounds, the molecular structure was confirmed by infrared and nuclear magnetic resonance spectroscopy.

The following examples are presented to further illustrate the invention.

EXAMPLE I

A mixture of 2.88 g (16.0 mmol) of olivetol, 2.45 g (16.1 mmol) of (+)-cis/trans-p-mentha-2,8-dien-1-ol, and 2 g of anhydrous magnesium sulfate was stirred with 100 ml of methylene chloride under $N_2$ atmosphere. After cooling in an ice bath, 1 ml (8.1 mmol) of freshly distilled boron trifluoride etherate was added. The mixture was stirred for 1.5 hr at 0° C and 5 g of anhydrous sodium bicarbonate was added. The stirring was continued until the color had faded, at which time the reaction mixture was filtered and evaporated to give a colorless gum (5 g). On the basis of gas-liquid chromatography, it contained 50 percent of $(-)$-$6a,1$-$0a$-trans-1-hydroxy-3-n-pentyl-6,6,9-trimethyl-$6a,7,8,$-$10a$-tetrahydrodibenzo[b,d]-pyran. One-half of this material was chromatographed on 150 g of magnesium silicate (100–200 mesh) packed in a 1 in. × 3 ft. column in petroleum ether (30°–40° ). It was eluted with petroleum ether followed by graded mixtures up to 2:98 of diethyl ether/petroleum ether. Fractions were combined and evaporated to give 0.77 g (31 percent) of material which was identical in all respects to an authenic sample: $[\alpha]_D$ $-176°$ $(CHCl_3)$, gas-liquid chromatographic purity >96 percent.

The above reaction was repeated on a larger scale using 28.8 g of olivetol, 24.5 g of (+)-cis/trans-p-mentha-2,8-dien-1-ol, 20 g of anhydrous magnesium sulfate and 1 l of methylene chloride. To the cooled (0° C) wellstirred solution was added 10.0 ml of boron trifluoride etherate. The temperature was maintained at 0° C and stirring was continued for 1.5 hr. Fifty grams of anhydrous sodium carbonate was added and the workup was continued as described above. After evaporation of the solvent, there was obtained 54 g of light brown gum. Gas-chromatographic analysis of an aliquot revealed that the mixture contained 42 percent of $(-)$ -$6a,10a$-trans-1-hydroxy-3-n-pentyl-6,6,9-trimethyl-$6a,7,8,10a$-tetrahydrodibenzo[b,d]pyran.

EXAMPLE II

A mixture of 2.88 g (16.0 mmol) of olivetol, 2.45 g (16.1 mmol) of (+)-cis/trans-p-mentha-2,8-dien-1-ol, 2 g of anhydrous magnesium sulfate, 100 ml of methylene chloride and 0.1 ml (0.8 mmol) of boron trifluoride etherate was stirred at 0° C for 1.5 hr. The reaction was quenched with 5 g of anhydrous sodium carbonate; the reaction mixture was filtered and the solvent removed on a rotary evaporator. On the basis of gas-chromatographic analysis, the reaction mixture contained 28 percent of 2-(p-mentha-1,8dien-3-yl)olivetol of Formula IV (R is n-pentyl), 47 percent of 4-(p-mentha-1,8-dien-3-yl)-olivetol of Formula V (R is n-pentyl) and 17 percent olivetol. The compounds were purified by column chromatography using magnesium silicate and graded diethyl ether/petroleum ether solvent mixtures.

50 mg of 4-(p-mentha-1,8-dien-3-yl)olivetol of Formula V was combined with 22 g of magnesium sulfate, 10 μl (0.08 mmol) of boron trifluoride etherate, and 1 ml of methylene chloride and stirred at 0° C. After 1.5 hr, gas-chromotographic analysis of the reaction mixture revealed the presence of 34 percent of (−)-6a,10a-trans-1-hydroxy-3-n-pentyl-6,6,9-trimethyl-6a,7,8,10a-tetraphdrobenzo[b,d]pyran. The reaction was quenched by the addition of sodium carbonate. The desired product can be isolated after workup and chromotography similar to that described hereinabove in Example I.

EXAMPLE III

A mixture of 74 g of threo-5-(1,2-dimethylheptyl)-resorcinol [prepared according to the procedure of Aaron and Ferguson, J. Org. Chem, 33, 684 (1968), 54 mg of (+)-cis/trans-p-mentha-2,8-dien-1ol, 1.8 microliter (0.014 mmol) of boron trifluoride etherate and 100 mg of anhydrous magnesium sulfate in 2 ml of methylene chloride was stirred at 0° C. After 20 min, an aliquot showed (gag-liquid chromotography) the presence of only the 2- and 4-p-mentha-1,8-dien-3-yl-5-(1,2-dimethylheptyl)resorcinols of Formulas IV and V in a ratio of 70:30, respectively. When no further change had occured after 17.5 hr at 0° C, 3 microliters (0.024 mmol) of boron trifluoride etherate was added and the temperature was maintained at 0° C. Three hours later, an aliquot was analyzed by gas-liquid chromotography and shown to contain 64 percent of (−)-6a,10a-trans-3-(1,2-dimethylheptyl)-1-hydroxy-6,6,9-trimethyl6a,7,8,10a-tetrahydrodibenzo[b,d]pyran. At this stage, the reaction can be quenched by the addition of sodium bicarbonate and stirring continued for 20 min. The desired product of (−)-6a,10a-trans-3-(1,2-dimethylheptyl)-1-hydroxy6,6,9trimethyl-6a,7,8,-10a-tetrahydrodibenzo[b,d]pyran can be purified according to the procedure described in Example I by column chromotography using graded diethyl ether/petroleum ether solvent mixtures.

EXAMPLE IV

A mixture of 277 mg (1.54 mmol) of olivetol, 237 mg (1.56 mmol) of (+)-cis/trans-p-mentha-2,8-dien-1-ol, 500 mg of anhydrous magnesium sulfate, 10 microliters (0.08 mmol) of boron trifluoride etherate and 10 ml of methylene chlrodie was stirred at 0° C for 50 min and stored overnight at 0° C. Gas-chromotrgraphic analysis of an aliquot of the reaction mixture revealed the presence of the following compounds: 36 percent of 2-(p-mentha-1,8-dien-3-yl)-olivetol of Formula IV (R is n-pentyl) and 35 percent of 4-(p-mentha-1,8-dien3yl)olivetol of Formula V (R is n-pentyl). An additional 100 μl (0.8 mmol) of boron trifluoride etherate was added, and the temperature was maintained at 0° C and stirring was continued. After 1.5 hr, the reaction mixture contained (gas-liquid chromotographic analysis) 43 percent of (−)-6a,10a-trans-1-hydroxy-3-n-pentyl-6,6,9-trimethyl-6a,7,8,10a-tetrahydrodibenzo[b,d]pyran. The reaction was quenched by addition of sodium bicarbonate. The desired compound can be isolated from the reaction mixture by preparative thin-layer chromotography.

EXAMPLE V 291 mg (1.61 mmol) of (+)-cis-/trans-p-mentha-2,8-dien-1-ol, 0.4 g of anhydrous magnesium sulfate, 0.1 ml (0.8 mmol) of boron trifluoride etherate and 10 ml of methylene chloride were combined and stirred at 25° c. After 10 minutes, the reaction mixture was analyzed by gas-liquid chromotography and shown to contain 44.3 percent of (−)-6a,10a-trans-1-hydroxy-3-n-pentyl-6,6,9-trimethyl-6a,7,8,10a-tetrahydrodibenzo[b,d]pyran. The product can be isolated according to the usual procedure of quenching the reaction, followed by filtration and evaporation of the solvent and column chromotography.

EXAMPLE VI

A mixture of 250 mg (1.39 mmol) of olivetol, 213 mg (1.40 mmol) of (+)-cis-trans-p-mentha-2,8-dien-1-ol, 700 mg of anhydrous magnesium sulfate and 10 ml of methylene chloride was vigorously stirred and cooled to −10° C. Boron trifluoride etherate (0.5 ml; 4 mmol) was added and the stirring was continued for 0.5 hr while the temperature was maintained at −10° C. A portion of the reaction mixtures was analyzed by gas-liquid chromotography and shown to contain 40 percent of (−)-6a,10a-trans-1-hydroxy-3-n-pentyl-6,6,9-trimethyl-6a,7,8,10a-tetrahydrodibenzo[b,d]pyran. Sodium carbonate was added to quench the reaction. The desired material can be isolated according to the procedure described hereinabove in Example I.

EXAMPLE VII

A mixture of 153 (0.85 mmol) of olivetol, 132 mg (0.87 mmol) of (+)-cis/trans-p-mentha-2,8-dien-1-ol and 200 mg of anhydrous magnesium sulfate in 5 ml of methylene chloride was stirred and cooled to ice bath temperature. Fifty microliters of anhydrous stannic chloride (0.111 g, 0.4 mmol) was added and stirring and cooling were continued. After 10 minutes, the reaction mixture was analyzed by gas-liquid chromotography and shown to contain 30 percent of (−)-6a,10a-trans-1-hydroxy-3-n-pentyl-6,6,9-trimethyl-6a,7,8,-10a-tetrahydrodibenzo[b,d]pyran. After quenching the reaction with sodium carbonate, the desired compound can be isolated from the reaction mixture according to the procedure described hereinabove in Example I.

EXAMPLE VIII

A mixture of 280 mg (1.84 mmol) of (+)-cis/trans-p-pentha-2,8-dien-1-ol, 345 mg (1.91 mmol) of olivetol and 350 mg of anhydrous magnesium sulfate in 7.1 ml of benzene was vigorously stirred and cooled to ice bath temperature. Gaseous boron trifluoride was bubbled into benzene at room temperature to prepare a saturated solution, and 2.9 ml of the saturated boron trifluoride solution (0.08 mmol BF₃) was added to the reaction mixture. After stirring and cooling for 2.5 hr, the reaction was analyzed by gas-liquid chromotography and shown to contain 30 percent of 2-(p-mentha-1,8-dien-3-yl)olivetol of Formula IV (R is n-pentyl) and 55 percent of 4-(p-mentha-1,8-dien-3-yl)olivetol of Formula V (R is n-pentyl). After quenching the reaction with sodium bicarbonate, the cannabidiols of Formulas IV and V can be isolated according to the procedure described hereinabove in the first part of Example II.

EXAMPLE IX

A solution of 248 mg (0.8 mmol) of 4-(p-mentha-1,8-dien-3-yl)-olivetol [prepared according to the procedure desecribed in Example II] in 5 ml of anydrous methylene chloride was vigorously stirred and cooled to a temperature of 0° C. Fifty microliters (0.4 mmol) of boron trilfluoride etherate was added and the mixture was stirred for 1.5 hr. while the temperature was maintained at 0° C. On the basis of gas-chromotographic analysis, the reaction mixture contained 30 percent of (−)-6a,10a-trans-1-hydroxy-3-n-pentyl-6,6,9-trimethyl-6a7,8,10a-tetrahydrodibenzo[b,d]pyran. Sodium carbonate was added to quench the reaction and stirring was continued. The desired product can be isolated by the usual workup which includes filtration of the reaction mixture and evaporation of the solvent, followed by preparative thinlayer chromotography on silica gel using a diethyl ether/petroleum ether solvent mixture.

EXAMPLE X

A mixture of 128 mg (1.03 mmol) of orcinol, 154 mg (1.01 mmol) of (+)-cis/trans-p-mentha-2,8dien-1-ol and 100 mg of anhydrous magnesium sulfate in 10 ml of methylene chloride was vigorously stirred and cooled to a temperature of 0° C. One hundred microliters (0.8 mmol) of boron trifluoride etherate was added and stirring was continued while the temperature was maintained at 0° C for 2 hr. The reaction was quenched by the addition of 500 mg of sodium bicarbonate. The inorganic materials were removed by filtration and the solvent was evaporated to give an amber gum. The gum was analyzed by gas-liquid chromatography and shown to contain several compound, the major product being 25 percent of the desired (+)-6a,10a-trans-1-hydroxy-3,6,6,9-tetramethyl-6a,7,8,10a-tetrahydrodibenzo[b,d]pyran. The desired material was partially separated by high pressure-liquid chromatography in a single pass through a column of silica get coated glass beads using a 3 percent diethyl ether/isooctane solvent system. Final purification can be accomplished by a second chromatography under similar conditions.

EXAMPLE XI

A mixture of 576 mg (3.20 mmol) of olivetol, 490 mg (3.22 mmol) of (+)-cis/trans-p-mentha-2,8-dien-1ol, 600 mg of anhydrous calcium sulfate and 20 ml of benzene was vigorously stirred and cooled to 10° C and 94 microliters (0.76 mmol) of boron trifluoride etherate was added. After stirring at 10° C for 1.5 hr, sodium carbonate (1.0 g) was added to quench the reaction. Gas-chromatographic analysis of the reaction mixture after quenching indicated the presence of 27 percent of 2-(p-mentha-1,8dien-3-yl)-olivetol of Formula IV (R is n-pentyl) and 49 percent of 4-(p-mentha-1,8-dien-3-yl)olivetol of Formula V (R is n-pentyl). The compounds can be isolated according to the procedure described hereinabove in the first part of Example II.

The foregoing detailed description has been given for clearness of understanding only, and no unnecessary limitations should be understood therefrom, as modifications will be obvious to those skilled in the art.

What is claimed is:
1. A process for the preparation of a compound of the formula

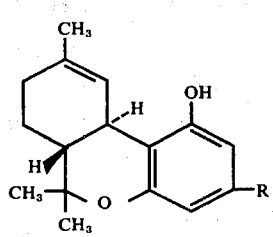

wherein R is hydrogen or a straight or branched alkyl containing 1 to 10 carbon atoms, comprising reacting a compound of the formula

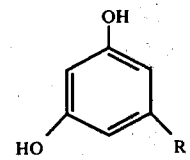

wherein R is as above,
with (+)-p-mentha-2,8-dien-1-ol in an inert organic solvent in a temperature range of −20° to +25° C in the presence of 0.04 to 0.40 mole per liter of an acid catalyst selected from the group consisting of boron trifluoride, boron trifluoride etherate, aluminum chloride, stannic chloride and antimony pentafluoride and an excess of a nonalkaline dehydrating agent selected from the group consisting of calcium sulfate, magnesium sulfate, sodium sulfate, calcium chloride, aluminum oxide, silica, and molecular sieves.

2. The process of claim 1, wherein said dehydrating agent is magnesium sulfate, said acid catalyst is boron trifluoride etherate at a concentration of 0.08 mole per liter, said inert organic solvent is methylene chloride and the reaction is carried out in a temperature range of −5° to +5° C.

3. The process of claim 1 wherein said acid catalyst is boron trifluoride.

4. The process of claim 3 wherein said acid catalyst is boron trifluoride etherate.

5. The process of claim 4 wherein said boron trifluoride etherate is at a concentration of 0.04 to 0.08 mole per liter.

6. The process of claim 1 wherein said dehydrating agent is magnesium sulfate.

7. The process of claim 3 wherein said dehydrating agent is magnesium sulfate.

8. The process of claim 4 wherein said dehydrating agent is magnesium sulfate.

9. The process of claim 5 wherein said dehydrating agent is magnesium sulfate.

10. A process for the preparation of a compound of the formula

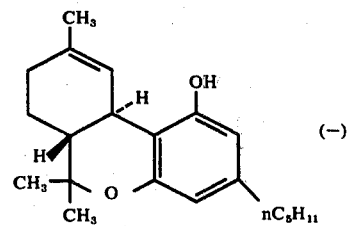

comprising reacting (+)-p-mentha-2,8-dien-1-ol and olivetol in an inert organic solvent in a temperature range of −20° to +25° C in the presence of 0.04 to 0.40 mole per liter of an acid catalyst selected from the group consisting of boron trifluoride, boron trifluoride etherate, aluminum chloride, zinc chloride, stannic chloride and antimony pentafluoride and an excess of a non-alkaline dehydrating agent selected from the group consisting of calcium sulfate, magnesium sulfate, sodium sulfate, calcium chloride, aluminum oxide, silica, and molecular sieves.

11. The process of claim 10 wherein said catalyst is boron trifluoride.

12. The process of claim 11 wherein said acid catalyst is boron trifluoride etherate.

13. The process of claim 12 wherein said boron trifluoride etherate is at a concentration of 0.04 to 0.08 mole per liter.

14. The process of claim 10 wherein said dehydrating agent is magnesium sulfate.

15. The process of claim 11 wherein said dehydrating agent is magnesium sulfate.

16. The process of claim 12 wherein said dehydrating agent is magnesium sulfate.

17. The process of claim 13 wherein said dehydrating agent is magnesium sulfate.

18. The process of claim 10, wherein said dehydrating agent is magnesium sulfate, said acid catalyst is boron trifluoride etherate at a concentration of 0.08 mole per liter, said inert organic solvent is methylene chloride and the reaction is carried out in the temperature range of −5° to +5° C.

* * * * *

UNITED STATES PATENT AND TRADEMARK OFFICE
CERTIFICATE OF CORRECTION

PATENT NO. : 4,025,516

DATED : May 24, 1977

INVENTOR(S) : Raj Kumar Razdan and Haldean Cloyce Dalzell

It is certified that error appears in the above-identified patent and that said Letters Patent are hereby corrected as shown below:

In the title, line 3, change "[B,D]-PYRANS" to --[B,D]PYRANS--; column 1, line 3, change "[B,D]-PYRANS" to --[B,D]PYRANS--; Column 1, line 7, change "form" to --from--; column 1, line 22, change "[b-d]" to --[b,d]; column 1, line 23, after "trans" insert a dash (-); column 1, line 39, change "enbable" to --enable--; column 1, line 43, change "3,560,224" to --3,560,528 and 3,668,224--; column 1, line 44, change "Petrizilka" to --Petrzilka--; column 1, line 46, change "den" to --dien--; column 1, line 49, change "Petrizilka" to --Petrzilka--; column 2, line 45, change "$\Delta^9$" to --$\Delta^8$--; column 3, line 27, change "tetrahydroccannabinol" to --tetrahydrocannabinol--; column 3, line 32, change "reaction" to --reacting--; column 4, line 25, change "Petrilka" to --Petrzilka--; column 4, line 35, change "compound" to --compounds--; column 4, line 37, insert a period (.) after "matography"; column 4, line 37, change "and" to --an--; column 5, line 64, change "the" to --The--; column 6, line 1, change "Forula" to --Formula--; column 6, line 18, change "timethyl" to --trimethyl--; column 6, line 19, change "drodibezo" to --drodibenzo--; column 6, line 24, change "rere" to --refer--; column 6, line 31, change "oxtyl" to --octyl--; column 6, line 54, change "In" to --The--; column 7, line 1, change "a" to --as--; column 7, line 3, after "sodium" insert --carbonate--; column 7, line 32, after "diethyl" insert --ether-; column 7, line 51, change "trifluoracetic" to --trifluoroacetic--; column 7, line 65, change "syntheiss" to --synthesis--; column 8, line 14, change "tifluoride" to --trifluoride--; column 9, line 1, change "dienopentyl" to --dineopentyl--; column 9, line 32, change "of" to --or--; column 9, line 58, change "the" to -- The--; column 10, line 6, change "compound" to --compounds--; column 10, line 9, change "autentic" to --authentic--; column 10, line 41, change "authenic" to --authentic--; column 10, line 68, insert a dash (-) after "1,8"; column 11, line 8, change "22g" to --22mg--; column 11, line 11, change "chromotographic" to --chromatographic--; column 11, line 14, change "tetraphdrobenzo" to --tetrahydrodibenzo--; column 11, line 17, change "chromotography" to --chromatography--; column 11, line 21, change "74 g" to --74 mg--; column 11, line 24, change "1 ol" to --1-ol--; column 11, line 28, change

UNITED STATES PATENT OFFICE
CERTIFICATE OF CORRECTION

Patent No. 4,025,516                    Dated May 24, 1977

Inventor(s) Raj Kumar Razdan and Haldean Cloyce Dalzell

It is certified that error appears in the above-identified patent and that said Letters Patent are hereby corrected as shown below:

"gag-liquid chromotography" to --gas-liquid chromatography--; column 11, line 32, change "occured" to --occurred--; column 11, line 36, change "chromotography" to --chromatography--; column 11, line 38, insert a dash (-) after "trimethyl"; column 11, line 42, insert a dash (-) after "hydroxy" and after "9"; column 11, line 45, change "chromotography" to --chromatography--; column 11, line 54, change "chlrodie" to --chloride--; column 11, line 55, change "chromotrgraphic" to --chromatographic--; column 11, line 59, change "dien3yl" to --dien-3-yl--; column 11, line 64, change "chromotographic" to --chromatographic--; column 12, line 2, change "chromotography" to --chromatography--; column 12, line 5, insert --(1.6 mmol) of olivetol, 243 mg-- after "291 mg"; column 12, line 10, change "chromotography" to --chromatography--; column 12, line 16, change "chromotography" to --chromatography--; column 12, line 20, change "cis-trans" to --cis/trans--; column 12, line 26, change "mixtures" to --mixture--; column 12, line 27, change "chromotography" to --chromatography--; column 12, line 35, insert --mg-- after "153"; column 12, line 42, change "chromo" to --chroma--; column 12, line 60, change "chromotogra" to --chromatogra--; column 13, line 5, change "desecribed" to --described--; column 13, line 5, change "anydrous" to --anhydrous--; column 13, line 8, change "trilfluoride" to --trifluoride--; column 13, line 10, change "chromoto" to --chromato--; column 13, line 13, insert a comma (,) after "6a"; column 13, line 18, change "chromotog" to --chromatog--; column 13, line 25, insert a dash (-) after "2,8"; column 13, line 35, change "chromotography" to --chromatography--; column 13, line 36, change "compound" to --compounds--; column 13, line 37, change "(+)" to --(-)--; column 13, line 40, change "chromotography" to --chromatography--; column 13, line 41, change "get" to --gel--; column 13, line 44, change "chromotography" to --chromatography--;

UNITED STATES PATENT OFFICE
CERTIFICATE OF CORRECTION

Patent No. 4,025,516                    Dated May 24, 1977

Inventor(s) Raj Kumar Razdan and Haldean Cloyce Dalzell

It is certified that error appears in the above-identified patent and that said Letters Patent are hereby corrected as shown below:

column 13, line 48, change "lol" to --1-ol--; column 13, line 55, change "chromotographic" to --chromatographic--; column 13, line 57, insert a dash (-) after "1,8"; column 14, first structure, change "(¯)" to --(-)--; column 15, line 14, insert --acid-- after "said".

Signed and Sealed this

Twenty-third Day of May 1978

[SEAL]

Attest:

RUTH C. MASON  
Attesting Officer

LUTRELLE F. PARKER  
Acting Commissioner of Patents and Trademarks